(12) United States Patent
Goodson, IV et al.

(10) Patent No.: US 7,585,836 B2
(45) Date of Patent: *Sep. 8, 2009

(54) BI-LATERAL LOCAL RENAL DELIVERY FOR TREATING CONGESTIVE HEART FAILURE AND FOR BNP THERAPY

(76) Inventors: Harry Burt Goodson, IV, 3596 Dickenson Common, Fremont, CA (US) 94538; Samir R. Patel, 366 Sierra Vista Ave., #6, Mountain View, CA (US) 94043; Craig A. Ball, 152 Belvedere Ave., San Carlos, CA (US) 94070; Jeffrey M. Elkins, 3 Eucalyptus Ct., Woodside, CA (US) 94601

( * ) Notice: Subject to any disclaimer, the term of this patent is extended or adjusted under 35 U.S.C. 154(b) by 0 days.

This patent is subject to a terminal disclaimer.

(21) Appl. No.: 11/129,101

(22) Filed: May 13, 2005

(65) Prior Publication Data

US 2005/0267010 A1 Dec. 1, 2005

Related U.S. Application Data

(60) Provisional application No. 60/571,057, filed on May 14, 2004.

(51) Int. Cl.
*A61K 38/00* (2006.01)
*A61M 25/00* (2006.01)
(52) U.S. Cl. .............................. 514/2; 530/300; 930/50
(58) Field of Classification Search ....................... None
See application file for complete search history.

(56) References Cited

U.S. PATENT DOCUMENTS

| | | |
|---|---|---|
| 1,696,018 A | 12/1928 | Schellberg |
| 2,499,045 A | 2/1950 | Walker et al. |
| 3,144,868 A | 8/1964 | Jascalevich |
| 3,455,298 A | 7/1969 | Anstadt |
| 3,516,408 A | 6/1970 | Montanti |
| 3,667,069 A | 6/1972 | Blackshear et al. |
| 3,730,186 A | 5/1973 | Edmunds, Jr. et al. |
| 3,791,374 A | 2/1974 | Guarino |
| 3,841,331 A | 10/1974 | Wilder et al. |
| 3,995,623 A | 12/1976 | Blake et al. |
| 4,248,224 A | 2/1981 | Jones |
| 4,309,994 A | 1/1982 | Grunwald |
| 4,345,602 A | 8/1982 | Yoshimura et al. |
| 4,407,271 A | 10/1983 | Schiff |
| 4,423,725 A | 1/1984 | Baran et al. |
| 4,459,977 A | 7/1984 | Pizon et al. |
| 4,490,374 A | 12/1984 | Bandurco et al. |
| 4,493,697 A | 1/1985 | Krause et al. |
| 4,536,893 A | 8/1985 | Parravicini |
| 4,546,759 A | 10/1985 | Solar |
| 4,554,284 A | 11/1985 | Stringer et al. |
| 4,636,195 A | 1/1987 | Wolinsky |
| 4,685,446 A | 8/1987 | Choy |
| 4,705,502 A | 11/1987 | Patel |
| 4,705,507 A | 11/1987 | Boyles |
| 4,712,551 A | 12/1987 | Rayhanabad |
| 4,714,460 A | 12/1987 | Calderon |
| 4,723,939 A | 2/1988 | Anaise |
| 4,753,221 A | 6/1988 | Kensey et al. |
| 4,781,716 A | 11/1988 | Richelsoph |
| 4,817,586 A | 4/1989 | Wampler |
| 4,834,707 A | 5/1989 | Evans |
| 4,840,172 A | 6/1989 | Augustine et al. |
| 4,846,831 A | 7/1989 | Skillin |
| 4,861,330 A | 8/1989 | Voss |
| 4,863,461 A | 9/1989 | Jarvik |
| 4,888,011 A | 12/1989 | Kung et al. |
| 4,902,272 A | 2/1990 | Milder et al. |
| 4,902,291 A | 2/1990 | Kolff |
| 4,906,229 A | 3/1990 | Wampler |
| 4,909,252 A | 3/1990 | Goldberger |
| 4,911,163 A | 3/1990 | Fina |
| 4,919,647 A | 4/1990 | Nash |
| 4,925,377 A | 5/1990 | Inacio et al. |
| 4,925,443 A | 5/1990 | Heilman et al. |
| 4,927,407 A | 5/1990 | Dorman |
| 4,927,412 A | 5/1990 | Menasche |
| 4,938,766 A | 7/1990 | Jarvik |
| 4,950,226 A | 8/1990 | Barron |
| 4,957,477 A | 9/1990 | Lundback |
| 4,964,864 A | 10/1990 | Summers et al. |
| 4,976,691 A | 12/1990 | Sahota |
| 4,976,692 A | 12/1990 | Atad |

(Continued)

FOREIGN PATENT DOCUMENTS

DE 4324637 A1 7/1993

(Continued)

OTHER PUBLICATIONS van der Zander, et al., Hypertension, 2003 (originally published on-line Dec. 2, 2002), 41, 119-123.*

(Continued)

*Primary Examiner*—Andrew D Kosar
*Assistant Examiner*—Satyanarayana R Gudibande

(57) ABSTRACT

The invention relates to systems and methods for local renal delivery of agents to subjects that are at risk for congestive heart failure and other conditions. The invention encompasses devices for renal drug delivery and methods of use.

27 Claims, 8 Drawing Sheets

U.S. PATENT DOCUMENTS

| | | |
|---|---|---|
| 4,990,139 A | 2/1991 | Jang |
| 4,995,864 A | 2/1991 | Bartholomew et al. |
| 5,002,531 A | 3/1991 | Bonzel |
| 5,002,532 A | 3/1991 | Gaiser et al. |
| 5,044,369 A | 9/1991 | Sahota |
| 5,053,023 A | 10/1991 | Martin |
| 5,059,178 A | 10/1991 | Ya |
| 5,067,960 A | 11/1991 | Grandjean |
| 5,069,662 A | 12/1991 | Bodden |
| 5,069,680 A | 12/1991 | Grandjean |
| 5,073,094 A | 12/1991 | Dorman et al. |
| 5,087,244 A | 2/1992 | Wolinsky |
| 5,089,019 A | 2/1992 | Grandjean |
| 5,098,370 A | 3/1992 | Rahat et al. |
| 5,098,442 A | 3/1992 | Grandjean |
| 5,112,301 A | 5/1992 | Fenton, Jr. et al. |
| 5,112,349 A | 5/1992 | Summers et al. |
| 5,119,804 A | 6/1992 | Anstadt |
| 5,129,883 A | 7/1992 | Black |
| 5,131,905 A | 7/1992 | Grooters |
| 5,135,474 A | 8/1992 | Swan et al. |
| 5,158,540 A | 10/1992 | Wijay et al. |
| 5,160,323 A | 11/1992 | Andrew |
| 5,163,910 A | 11/1992 | Schwartz et al. |
| 5,167,628 A | 12/1992 | Boyles |
| 5,180,364 A | 1/1993 | Ginsburg |
| 5,205,810 A | 4/1993 | Guiraudon et al. |
| 5,226,888 A | 7/1993 | Arney |
| 5,256,141 A | 10/1993 | Gencheff et al. |
| 5,257,974 A | 11/1993 | Cox |
| 5,282,784 A | 2/1994 | Willard |
| 5,290,227 A | 3/1994 | Pasque |
| 5,292,309 A | 3/1994 | Van Tassel et al. |
| 5,308,319 A | 5/1994 | Ide et al. |
| 5,308,320 A | 5/1994 | Safar et al. |
| 5,312,343 A | 5/1994 | Krog et al. |
| 5,320,604 A | 6/1994 | Walker et al. |
| 5,326,374 A | 7/1994 | Ilbawi et al. |
| 5,328,470 A | 7/1994 | Nabel et al. |
| 5,332,403 A | 7/1994 | Kolff |
| 5,345,927 A | 9/1994 | Bonutti |
| 5,358,519 A | 10/1994 | Grandjean |
| 5,364,337 A | 11/1994 | Guiraudon et al. |
| 5,370,617 A | 12/1994 | Sahota |
| 5,383,840 A | 1/1995 | Heilman et al. |
| 5,397,307 A | 3/1995 | Goodin |
| 5,411,479 A | 5/1995 | Bodden |
| 5,421,826 A | 6/1995 | Crocker et al. |
| 5,429,584 A | 7/1995 | Chiu |
| 5,453,084 A | 9/1995 | Moses |
| 5,464,449 A | 11/1995 | Ryan et al. |
| 5,476,453 A | 12/1995 | Mehta |
| 5,478,331 A | 12/1995 | Heflin et al. |
| 5,484,385 A | 1/1996 | Rishton |
| 5,505,701 A | 4/1996 | Anaya Fernandez de Lomana |
| 5,509,428 A | 4/1996 | Dunlop |
| 5,536,250 A | 7/1996 | Klein et al. |
| 5,558,617 A | 9/1996 | Heilman et al. |
| 5,569,296 A | 10/1996 | Marin et al. |
| 5,599,306 A | 2/1997 | Klein et al. |
| 5,609,628 A | 3/1997 | Keranen |
| 5,613,949 A | 3/1997 | Miraki |
| 5,613,980 A | 3/1997 | Chauhan |
| 5,617,878 A | 4/1997 | Taheri |
| 5,643,171 A | 7/1997 | Bradshaw et al. |
| 5,643,215 A | 7/1997 | Fuhrman et al. |
| 5,669,924 A | 9/1997 | Shaknovich |
| 5,702,343 A | 12/1997 | Alferness |
| 5,713,853 A | 2/1998 | Clark et al. |
| 5,713,860 A | 2/1998 | Kaplan et al. |
| 5,720,735 A | 2/1998 | Dorros |
| 5,755,779 A | 5/1998 | Horiguchi |
| 5,762,599 A | 6/1998 | Sohn |
| 5,766,151 A | 6/1998 | Valley et al. |
| 5,776,190 A | 7/1998 | Jarvik |
| 5,797,876 A | 8/1998 | Spears et al. |
| 5,807,311 A | 9/1998 | Palestrant |
| 5,807,895 A | 9/1998 | Stratton et al. |
| 5,817,046 A | 10/1998 | Glickman |
| 5,902,229 A | 5/1999 | Tsitlik et al. |
| 5,902,336 A | 5/1999 | Mishkin |
| 5,913,852 A | 6/1999 | Magram |
| 5,928,132 A | 7/1999 | Leschinsky |
| 5,935,924 A | 8/1999 | Bunting et al. |
| 5,968,013 A | 10/1999 | Smith et al. |
| 5,971,910 A | 10/1999 | Tsitlik et al. |
| 5,984,955 A | 11/1999 | Wisselink |
| 6,001,079 A | 12/1999 | Pourchez |
| 6,013,054 A | 1/2000 | Jiun Yan |
| 6,039,721 A | 3/2000 | Johnson et al. |
| 6,068,629 A | 5/2000 | Haissaguerre et al. |
| 6,077,256 A | 6/2000 | Mann |
| 6,086,527 A | 7/2000 | Talpade |
| 6,086,557 A | 7/2000 | Morejohn et al. |
| 6,096,073 A | 8/2000 | Webster et al. |
| 6,117,117 A | 9/2000 | Mauch |
| 6,117,156 A | 9/2000 | Richter et al. |
| 6,142,973 A | 11/2000 | Carleton et al. |
| 6,143,002 A | 11/2000 | Vietmeier |
| 6,156,016 A | 12/2000 | Maginot |
| 6,165,120 A | 12/2000 | Scheich, Jr. et al. |
| 6,190,349 B1 | 2/2001 | Ash et al. |
| 6,210,380 B1 | 4/2001 | Mauch |
| 6,251,133 B1 | 6/2001 | Richter et al. |
| 6,261,273 B1 | 7/2001 | Ruiz |
| 6,261,316 B1 | 7/2001 | Shaolian et al. |
| 6,287,277 B1 | 9/2001 | Yan |
| 6,287,608 B1 | 9/2001 | Levin et al. |
| 6,325,826 B1 | 12/2001 | Vardi et al. |
| 6,387,037 B1 | 5/2002 | Boiling et al. |
| 6,390,969 B1 | 5/2002 | Boiling et al. |
| 6,468,241 B1 | 10/2002 | Gelfand et al. |
| 6,475,208 B2 | 11/2002 | Mauch |
| 6,482,211 B1 | 11/2002 | Choi |
| 6,494,875 B1 | 12/2002 | Mauch |
| 6,508,787 B2 | 1/2003 | Erbel et al. |
| 6,514,226 B1 | 2/2003 | Levin et al. |
| 6,533,747 B1 | 3/2003 | Polschegg et al. |
| 6,540,779 B2 | 4/2003 | Richter et al. |
| 6,592,567 B1 | 7/2003 | Levin et al. |
| 6,595,959 B1 | 7/2003 | Statienko et al. |
| 6,669,718 B2 | 12/2003 | Besselink |
| 6,699,231 B1 | 3/2004 | Sterman et al. |
| 6,733,474 B2 | 5/2004 | Kusleika |
| 6,749,598 B1 | 6/2004 | Keren et al. |
| 6,749,628 B1 | 6/2004 | Callol et al. |
| 6,884,258 B2 | 4/2005 | Vardi et al. |
| 6,887,258 B2 | 5/2005 | Denison et al. |
| 6,911,039 B2 | 6/2005 | Shiu et al. |
| 6,945,992 B2 | 9/2005 | Goodson et al. |
| 6,994,700 B2 | 2/2006 | Elkins et al. |
| 7,104,981 B2 | 9/2006 | Elkins et al. |
| 7,381,204 B2 | 6/2008 | Wilson et al. |
| 7,470,252 B2 | 12/2008 | Mickley et al. |
| 2001/0029349 A1 | 10/2001 | Leschinsky |
| 2001/0031907 A1 | 10/2001 | Downey et al. |
| 2002/0022857 A1 | 2/2002 | Goldsteen et al. |
| 2002/0090388 A1 | 7/2002 | Humes et al. |
| 2002/0091355 A1 | 7/2002 | Hayden |
| 2002/0165574 A1 | 11/2002 | Ressemann et al. |
| 2002/0169413 A1 | 11/2002 | Keren et al. |
| 2003/0050600 A1 | 3/2003 | Ressemann et al. |
| 2003/0069468 A1 | 4/2003 | Bolling et al. |
| 2003/0100919 A1 | 5/2003 | Hopkins et al. |

| | | | |
|---|---|---|---|
| 2003/0144636 A1 | 7/2003 | Liu | |
| 2003/0153898 A1 | 8/2003 | Schon et al. | |
| 2003/0181856 A1 | 9/2003 | Goldman | |
| 2003/0220664 A1 | 11/2003 | Petrick et al. | |
| 2004/0002730 A1 | 1/2004 | Denison et al. | |
| 2004/0044302 A1 | 3/2004 | Bernard et al. | |
| 2004/0059179 A1* | 3/2004 | Maguire et al. | 600/16 |
| 2004/0064089 A1 | 4/2004 | Kesten et al. | |
| 2004/0097900 A1 | 5/2004 | Keren et al. | |
| 2004/0111148 A1 | 6/2004 | Goodson | |
| 2004/0117003 A1 | 6/2004 | Ouriel et al. | |
| 2004/0167415 A1 | 8/2004 | Gelfand et al. | |
| 2004/0167463 A1 | 8/2004 | Zawacki et al. | |
| 2004/0254236 A1 | 12/2004 | Dong et al. | |
| 2005/0027305 A1 | 2/2005 | Shiu et al. | |
| 2005/0197624 A1 | 9/2005 | Goodson et al. | |
| 2005/0245882 A1 | 11/2005 | Elkins et al. | |
| 2005/0245892 A1 | 11/2005 | Elkins et al. | |
| 2005/0267010 A1 | 12/2005 | Goodson et al. | |
| 2006/0030814 A1 | 2/2006 | Valencia et al. | |
| 2006/0036218 A1 | 2/2006 | Goodson et al. | |
| 2006/0047266 A1 | 3/2006 | Elkins et al. | |
| 2006/0069323 A1 | 3/2006 | Elkins et al. | |
| 2006/0079836 A1 | 4/2006 | Holman et al. | |
| 2006/0079859 A1 | 4/2006 | Elkins et al. | |
| 2006/0149350 A1 | 7/2006 | Patel et al. | |
| 2006/0259066 A1 | 11/2006 | Euteneuer | |
| 2007/0053904 A1 | 3/2007 | Kirst et al. | |

FOREIGN PATENT DOCUMENTS

| | | |
|---|---|---|
| EP | 654283 A1 | 11/1994 |
| EP | 884064 A2 | 5/1998 |
| GB | 2239675 A | 7/1994 |
| WO | WO 97/11737 | 4/1997 |
| WO | WO 98/03213 A1 | 1/1998 |
| WO | WO 98/17347 A1 | 4/1998 |
| WO | WO 98/52639 A1 | 11/1998 |
| WO | WO 99/33407 A1 | 12/1998 |
| WO | WO 99/22784 A1 | 5/1999 |
| WO | WO 99/51286 A1 | 10/1999 |
| WO | WO 00/41612 A2 | 1/2000 |
| WO | WO 01/83016 | 4/2001 |
| WO | WO 01/37882 A | 5/2001 |
| WO | WO 01/41861 A1 | 6/2001 |
| WO | WO 01/97687 | 12/2001 |
| WO | WO 01/97717 | 12/2001 |
| WO | WO 01/97878 A1 | 12/2001 |
| WO | WO 01/97879 A1 | 12/2001 |
| WO | WO 2004/026370 A | 4/2004 |
| WO | WO 2004/032791 * | 4/2004 |
| WO | WO 2004/032791 A | 4/2004 |
| WO | WO 2005/002660 A1 | 1/2005 |
| WO | WO 2005/014100 A1 | 2/2005 |

OTHER PUBLICATIONS

Gianello, et al., Clinical Transplantation, 1995, 9, 481-489.*
Venkataraman, Crit. Care Clin., 2005, 21(2), 281-289 (Abstract).*
Geisburg, et al., Cleveland Clinic Journal of Medicine, 2006, 73, 485-491.*
[Retrived from] http://www.nutropin.com/patient/5_1_renal_insufficiency.jsp[Retrived on Nov. 13, 2006].*
[Retrived from] http://www.umm.edu/altmed/ConsConditions/DiabetesMellituscc.html, clearly states that currently there is no proven way to prevent Type I diabetes mellitus retrived on Nov. 13, 2006.*
Farncombe, Support Care Cancer, 1997, 5, 94-99.*
[Retrived from] http://encarta.msn.com/encnet/features/dictionary/DictionaryResults.aspx?refid=1861737040, 2007, 1 page, [Retrieved on Apr. 18, 2007].*
Blaine, 1986, Federation Proc., 45, 2122-2127.*
Venkataraman, Crit. Care Clin., 2005, 21(2), 281-289.*
Van der Zander, et al., 2003, Hypertension, 41, 119-123.* http://www.nutropin.com/patient/5_1_renal_insufficiency.jsp.*
http://www.umm.edu/altmed/ConsConditions/DiabetesMellituscc.html.*
"FDA Form 510(K) on Related Correspondence for Advanced Equipment Development, Inc."
Agostoni et al. Sustained Benefit from Ultrafiltration in Moderate Congestive heart failure Cardiology 2001:96 183-189.
Akaba, N. et al.; "A Cylinder-Shaped Balloon Catheter for the Management of Dissecting Aneurysms in Acute Stage," Herz, vol. 17, No. 6, pp. 390-393, Dec. 1992. Abstract Only.
Aspelin, et al., "Nephrotoxic Effects in High-Risk Patients Undergoing Angiography," N Engl J Med, Feb. 2003, vol. 348, No. 6, pp. 491-499.
Bakris, et al., Renal Hemodynamics in Radiocontrast Medium-Induced Renal Dysfunction etc. Kidney International, vol. 56 pp. 206-210 (1999).
Beregi, et al., "Doppler Flow Wire Evaluation of Renal Blood Flow Reserve in Hyertenstive Patient With Normal Renal Arteries," Cardiovascular and Interventional Radiology, vol. 23, pp. 340-346 (2000).
Bergey, E.A. et al.; "Transhepatic Insertion of Vascular Dialysis Catheters in Children: A Safe, Life-Prolonging Procedure," Pediatr. Radiol., vol. 29, No. 1, pp. 42-50, Jan. 1999. Abstract Only.
Bischoff, W. et al.; "Modified in Suty Perfusion of the Kidney Using Balloon Catheters," vol. 94, No. 30, pp. 1695-1697, Oct. 21, 1976. Abstract Only.
Briguori et al., "Contrast Agent-Assocaited Nephrotoxicity," Progress in Cardiovascular Diseases, 45;6(2003): 493-503.
Canaud, B. et al.; "Temporary Vascular Access for Extracorporeal Renal Replacement Therapies in Acute Renal Failure Patients," Kidney Int. Suppl., vol. 66, pp. S142-S150, May, 1998. Abstract Only.
Chatterjee, "Refractory heart failure-drugs and devices", European Heart Journal, 2001, 22:2227-2230.
Chu, et al. "Fenoldopam in the Prevention of Contrast Media-Induced Acute Renal Failure," The Annals of Pharmacotherapy, 35:1278-1282 (2001).
Cohn, Jay N.; "The Management of Chronic Heart Failure," The New England Journal of Medicine, pp. 490-498. Aug. 15, 1996.
Darves, "ASHP: Perioperative Fenoldopam Improves Renal Function During Major Surgery," Retrieved from the Internet [Online]: www.pslgroup.com/dg/225C72.htm, Dec. 19, 2002.
Del Greco, The Kidney in Congestive Heart Failure, Modern Concepts of Cardiovascular, Sep. 1975, vol. 44, No. 9, pp. 47-52.
D'Elia et al., Nephrotoxicity from Angiographic Contrast Material, "A prospective Study," Am J Med, May 1982, vol. 72, pp. 719-725.
Diaz-Sandoval, et al., "Acetylcysteine to Prevent Angiography-Related Renal Tissue Injury," The American Journal Journal of Cardiology, Feb. 1, 2002: vol. 89, pp. 356-358.
Drescher, et al., Prevention of Contrast Medium-Induced Renal Vasospasm by Phosphodiesterase Inhibition, Ivest Radiol 1998; 33:858-862.
Eisenberg, et al., Renal Failure After Major Angiography Can be Avoided with Hydration, AJR, May 1981; 136:859-861.
Eisenberg, et al., Renal Failure After Major Angiography, Am J Med, Jan. 1980, vol. 68, pp. 43-46.
Eisenberger, F. et al.; "Transfemoral Cannulation of the Renal Vessels. Diagnostic and Therapeutic use in Urology," Urologe [A], vol. 16, No. 1, pp. 1-5, Jan. 1977. Abstract Only.
Elkayam, et al., Renal Hemodynaic Effects of Vasodilation with Nifedipine and Hydralazine in Patients With Heart Failure, JACC Dec. 1984; vol. 4, No. 6, pp. 1261-1267.
Elkayam, et al., Renal Vasodilatory Effect of Endothelial Stimulation in Patients with Chronic Congestive Heart Failure, J Am Coll Cardiol 1996;28:176-182.
Fox, S.L.; "Mechanisms of Contraction," Human Physiology, Fourth Edition, pp. 300-323.
Freeman, et al., "Nephopathy Requiring Dialysis After Percutaneous Coronary Intervention and the Critical role of an Adjusted Contrast Dose," Am J Cardiol, vol. 90, (Nov. 15, 2002) pp. 1068-1073.
Garwood, Susan et al.; "Renal Preservation Strategies for High Risk Patients,"University of Chico School Medicine, Cover Page, Table of Contents Page, pp. 1-19, 1998.

Gerlach, et al., "Contrast Medium-Induced Nephrotoxicity: Pathophysiology and Prevention," *Pharmacotherapy*, 2000, 20(5):540-548.

Greco, B.A. et al.; "Atherosclerotic Ischemic Renal Disease," Am. J. Kidney Dis., vol. 29, No. 2, pp. 167-187, Feb. 1997. Abstract Only.

Gruberg, et al. The prognostic implications of further renal deterioration within 48 h of interventional etc. J AM Coll Cardiol 2000, 20(5):540-548.

Halpenny et al. The effects of fendolopam on renal blood flow and tubular function during aortic cross-clamping in anaesthetized dogs, EUR J Anaetestheisol, Aug. 2000: 17(8); 491-8 Abstract.

Heyman, et al., Pathophysiology of Radiocontract Nephropathy, A Role for Medullary Hypoxia, Invest Radiol, 1999; 34:685-691.

Hobbs, et al., "An Update on Nesiritide for Treatment of Decompensated Heart Failure," *Exp. Opin. Invest. Drugs*, 2001, 10(5):935-942.

Houghton, et al., "Basal and Reserve Renal Artery Blood Flow: Effect of Endothelium-Dependent and Independent Vasoactive Agonists and Radiographic Contrast Medium in Two Patients", *J invas Cardiol* 2000, 12: 211-215.

Hunter et al., "Preventing Contrast-Induced Nephropathy with Fenoldopam," Techniques in Vascular and Interventional Radiology. 2001. 4:1:53-56.

Iannone, L.D. et al.; "Effect of Primary Balloon Expandable Renal Artery Stents o Long-Term Patency, Renal Function, and Blood Pressure in Hypertensive and Renal Insufficient Patients with Renal Artery Stenosis," Cathet. Cardiovasc. Dign., vol. 37, No. 3, pp. 243-250, Mar. 1996. Abstract Only.

Jacobs, M.J. et al.; "Reduced Renal Failure Following Thoracoabdominal Aortic Aneurysm Repair by Selective Prefusion," Eur. J. Cardiothorac. Surg., vol. 14, No. 2, pp. 201-205, Aug. 1998. Abstract Only.

Katsumata T. et al.' "Newly-Developed Catheter for Cardio-Renal Assist During Intraaortic Balloon Counterpulsation," Kyobu Geka, vol. 46, No. 9, pp. 767-770, Aug. 1993. Abstract Only.

Kay, et al., Acetylcysteine for Prevention of Acute Deterioration of Renal Function Following Elective Coronary Angiography and Intervention, *JAMA*, vol. 289 No. 5, (Feb. 5, 2003).

Kehrer et al.; "Construction and Experimental Application of a Catheter for Selective Arterial Kidney Perfusion in Situ," Urological Research, vol. 13, pp. 85-89, 1985.

Kim, et al., Fluriscopic Landmarks for Optimal Visualization of the Proximal Renal Arteries, JVIR, 10:37-39 (1999).

Kini et al. A protocol for Prevention of Radiographic contrast Nepropathy etc. Catheterization and Cardiovascular Interventions 2002, 55:169-173.

Kini et al. Managing the High-Risk Patient: Experience with Fenoldopam etc. Rev. Cardiovas Med 2001:2(suppl 1) S19-S25.

Kobayashi, A. et al.; "Experimental Study on the Usefulness of the Autoperfusion Balloon Catheter in Maintaining the Blood Supply to the Distal Organs," Nippon Igaku Hoshasen Gakkai Zasshi, vol. 52, No. 5, pp. 682-684, May 25, 1992. Abstract Only.

Kou-Gi Shyu et al., "Acetylcysteine Protects Against Acute Renal Damage in Patients with Abnormal Renal Function Undergoing a Coronary Procedure," The Journal of the American College of Cardiology, 2002; 40:8.

Lass, et al., Cardiocascular and Renal Hemodynamic Effects of Intravenous Infusions of the Selective DA1 Agonist ec., Circulation 1988; 78:1310-1315.

Levin, Howard, R. et al.; "Reversal of Chronic Ventricular Dilation in Patients with End-Stage Cardiomyopathy by Prolonged Mechanical Unloading," vol. 91, No. 11, pp. 2727-2748, Jun 1, 1995.

Linden, R.J. et al.; "The Nature of the Atrial Receptors Responsible for a Reflex Decrease in Activity in Renal Nerves of the Dog," The Physiological Society, pp. 31-40, 1980.

Madyoon, "Clinical Experience with the Use of Fenoldopam for Prevention of Radiocontrast Hephropathy etc," *Rev Cardiovasc Med.* 2001, 2(suppl 1 ); S26-S30.

Madyoon, Use of Fenoldopam to Prevent Radiocontrast Nephropathy etc. Catherization and Cardiovascular Interventions 2001, 53:341-345.

Margulies, et al., Induction and Prevention Radiocontrast-Induced Nephropathy in Dogs with Heart Failure, Kidney Int. 1990; vol. 38:1101-1108.

Margulies, et al., Intra-Arterial Atrial Natriuetic Factor (ANF) Attenuates Radiocontrast-Induced etc., Renal Pathology, unknown date, pp. 666, Abstract only.

Masaki, Z. et al.; "In Situ Perfusion by Retrograde Cannulation of a Tumor Artery for Nephron-Sparing Surgery," Int. J. Urol, vol. 2, No. 3, pp. 161-165, Jul. 1995. Abstract Only.

Mason, et al., Renal Dysfunction After Arteriography, JAMA, 1985;253:1001-1004.

Mathis, J. M. et al.; "Use of Guide Catheter as a Temporary Stent During Microcatheter Intervention," AJNR Am. J. Neuroradiol, vol. 19, No. 5, pp. 932-933, May, 1998. Abstract Only.

Mathur et al., The effects of fenoldopam, a selective dopamine receptor agonist, on renal hemodynamics etc. Abstract only. Crit Cre Med Sep. 1999: 27(9) 1832-1837.

Mathur, "The Role of the DA1 Receptor Agonist Fenoldopam in the Management of Critically Ill, Transplant, and Hypertensive Patients," *Reviews in Cardiovascular Medicine*, 2003;4(Supp 1):S35-S40.

Mccarthy, Animal Models in Medical Device Development and Qualification, Charles River Laboratories, vol. 10(2) 1997.

Mccullough, et al., Acute Renal Failure after Coronary Intervention: Incencence, Risk Factors, and Relationship to Mortality, Am J Med. 1997; 103:368-375.

Mehran, et al., "A Risk Score for Prediction of Contrast Induced nephropathy After Percutaneous Coronary Intervention," Retrieved from the Internet [Online]: www.abstractsonline.com/viewer, Mar. 31, 2003.

Mehran, et al., "Radiocontrast-Induced Acute Renal Failure: Allocations and Outcomes," *Rev Cardiovasc Med* 2001;2(suppl1):S9-S13.

Middleton, J. P.; "Ischemic Disease of the Kidney: How and Why to Consider Revascularization," J. Nephrol., vol. 11, No. 3, pp. 123-136, May-Jun. 1998. Abstract Only.

Miller, et al., "Effects of Fenoldopam on Renal Blood Flow and Tubular Function Following Supraerenal Aortic Cross-Clamping," *Ann Vasc Surg*, 2003, Published online Oct. 23, 2003. Abstract Only.

Mintz, et al., "Radiocontrast-Induced Nephropathy and Percutaneous Coronary Intervention," *Expert Opin. Pharmacother.*, 2003; 4(5):639-652.

Mueller et al. Prevention of Contrast Media Associated Nephropathy, Arch Intern Med, Feb. 2002, vol. 162 pp. 329-336.

Murray et al., "Clinical Anesthesiology: Third Edition." McGraw-Hill Professional. New York. 2002.

Nohria et al. Medical Management of Advanced Heart Failure, JAMA, Feb. 6, 2002, vol. 162, pp. 628-640.

Novick, A.C.; "Atherosclerotic Ischemic Nephropathy. Epidemiology and Clinical Considerations," Urol. Clin. North Am., vol. 21, No. 2, pp. 195-200, May 1994. Abstract Only.

Paganini, et al., "Severity Scores and Outcomes With Acute Renal Failure in the ICU Setting," *Contrib Nephrol*, 2001; 132: 181-195.

Parfrey, et al., Contrast Material-Induced Renal Failure in Patients with Diabetes Mellitus, Renal Insufficiency, or Both, N Engl J Med, 1989, 320:149-153.

Patel, et al., Intravenous Fenoldopam Infusion in Severe Heart Failure, Cardiovasc Drugs Ther 1993; 7:97-101.

Pharmacy and Therapeutics Committee, Fenoldopam Mesylate (Corlopam) Usage Guidelines:, Clinical Pharmacy Associaates, Inc. Feb. 2001. http://www.clinpharm.com/client_data/productfiles/fenoldopam%20usage%20guidelines.pdf Access Nov. 29, 2007.

Pierce, "Fenoldopam (Corlopam) DUE", Pharmacy & Therapeutics Committee, Jan. 2002, http://prodruginfo.com/Formulary/DUE/fenolddue.pdf, Accessed Sep. 12, 2007.

Postma, C.T. et al.; "Treatment of Renal Artery Stenosis with Intra-Arterial Stents," Ned Tijdshr Genneeskd., vol. 142, No. 39, pp. 2132-2137, Sep. 26, 1998. Abstract Only.

Ramanathan, et al., Ameliorating Contrast-Induced Nephropathy, Journal of Invasive Cardiology, Nov. 2001, Retrieved from the Internet [Online]: www.invasivecardiology.comlfic_20011/jic_200111f6.html.

Rebeiz, et al., "Radiocontrast Nephropathy: a Time for Affirmative Action, *J Invasive Cardiology*," Jan. 2003; vol. 15, No. 1, pp. 23-24.

Rihal, et al., "Incidence and Prognostic Importance of Acute Renal Failure After Percutaneous Coronary Intervention," *Circulation*, (May 14, 2002),105:2259-2264.

Ritchie, et al., "Use of nonionic or Low Osmolar Contrast Agents in Cardiovascular Procedures," Retrieved from the Internet [Online] www.acc.org/clinical/position/72543.htm, Jan. 22, 2003.

Robinson, et al., "Congestive Heart Failure: Targeted Drug Therapy and Invasive Interventions", Retrieved from the Internet [Online] www.speroff.com/articleslTextbook/66_CHF2.htm, printed Sep. 4, 2002.

Rudnick, et al., Nephrotoxicity of Ionic and Noionic Contrast Media in 1196 Patients: A Randomized Trial, Kidney International, 1995; 47:254-261.

Schwab, et al., Contrast Nephrotoxicity: A Randomized Controlled Trial of a Nonionic and an Ionic Radiographic Contrast Agent, N Engl J Med, 1989, 320:149-153.

Seiter, H. et al.; "Modified T-Catheter and its use for Transvenous Hypothermic in Situ Perfusion in the Surgical Restoration of the Kidney with Staghorn calculi," Z. Uro Nephrol., vol. 76, No. 6, pp. 403-406, Jun. 1983. Abstract Only.

Sheifer, "Sex Differences in Coronary Atery Size", American Heart Journal, 2000; 139(4):649-653.

Shusterman, et al., Fenoldopam, But Not Nitroprusside, Improves Renal Function etc. Am J of Medicine, 95:161-168 (1993).

U.S. Appl. No. 09/165,333—Leschinsky, Boris—"Method and Apparatus for Treating Aneurysms".

Solomon, et al., Effects of Saline, Mannitol, and Furosemide on Accute Decreases in Renal Function etc., N Engl J Med 1994; vol. 331 No. 21 pp. 1416-1420.

Stevens, et al., A Prospective Randomized Trail of Prevention Measures in Patients at High Risk for Contrast Nephropathy, J Am Coll Cardiol, 1999; 33:403-411.

Strick, et al., Direct Measurement of Renal Medullary Blood Flow in the Dog, Am J. Physiol. 267 (Regulatory Integrative Comp. Physiol. 36): R253-R2259, 1994.

Suehiro, et al., "Selective Renal Vasodilation and Active Renal Artery Perfusion Improve Renal Function in Dogs with Acute Heart Failure," *The Journal of Pharmacology and Experimental Therapeutics*, vol. 298, No. 3 pp. 1154-1160 (2001).

Taliercio, et al., Risks for Renal Dysfunction with Cardiac Angiography, Annals of Internal Medicine, 1986; 104:501-504.

Thatipelli et al., "CT Angiography of Renal Artery Anantomy for Evaluating Embolic Protection Devices." Journal of Vascular and Interventional Radiology. 2007; 18(7): 842-846.

Thomas, et al., Glomerrular Filtration Dynamics During Renal Vasodilation etc. Am. J. Physiol. 244:F606-F611 (1983).

Thomas, et al., Influence of Bradykinin and Papaverine on Renal etc., Renal Physiology, Basel 5:197-205 (1982).

Tumlin et al., "Fenoldopam Mesylate Blocks Reductions in Renal Plasma Flow After Radiocontrast Dye Infusion: A Pilot Trial in the Prevention of Contrast Nephropathy," The American Heart Journal, 2002; 143:5:894-903.

UIC College Of Pharmacy, "Is Fenoldopam (Corlopam) Useful for the Prevention Of Contrast Media Associated Nephrotoxicity?", Retrieved from the Internet [Online] www.uic.edu/pharmacy/services/di/fenoldopam.htm, Jan. 2003.

Umrani et al., Beneficial effects of fenoldopam treatment on renal function in streptozotocin-induced diabetic rats, Clin Exp Hypertens, Apr. 24, 2002 (3): 207-19 Abstract only.

Vari, et al., Induction, Prevention and Mechanisms of Contrast Media-Induced Acute Renal Failure, Kidney International, 1988; 33:669-707.

Walker, H.S. et al.; "Use of a Balloon-Tipped Profusion Catheter for Renal Preservation During Suprarenal Abdominal Aortic Operations," J. Vasc. Surg., vol. 2, No. 2, pp. 337-339, Mar. 1985. Abstract Only.

Weisberg et al., Risk of radiocontrast nephropathy in patients with and without diabetes mellutus, Kidney International, 1994, 45:259-265.

White, C.J. et al.; "Renal Artery Stent Placement: Utility in Lesions Difficult to Treat with Balloon Angioplasty," Am. Coll. Cardiol., vol. 30, No. 6, pp. 1445-1450, Nov. 15, 1997. Abstract Only.

Williams, D.M. et al.; "Design and Testing of a High-FLo2 Autoperfusion Catheter: An Experimental Study," J. Vasc. Interv. Radiol., vol. 3, No. 2, pp. 285-290, May 1992. Abstract Only.

Zacherl, et al. Periarterial Papverine Applications Improves Intraoperative Kidney Function etc. Journal of Surgical Research 103:268-271 (2002).

Madyoon et al., "Fenoldopam for prevention of contrast-induced renal dysfunction in a high risk angiography population: A historically-controlled case series", Circulation vol. 104, No. Suppl. 17, XP009098219, Oct. 23, 2001, p. II-185.

Mathur, V.S., "Pathophysiology of radiocontrast nephropathy and use of fenoldopam for its prevention", Reviews in Cardiovascular Medicine, vol. 2, No. Suppl. 1, 2001, pp. 54-58, XP009098238.

Stone, G.W. et al., "Designand rationale of Contrast—a prospective, randomized, placebo-controlled trial of fenoldopam mesylate for the prevention of radiocontrast nephropathy", Reviews in Cardiovascular Medicine, vol. 2, No. Suppl. 1, 2001, pp. 531-536, XP009098217.

Tumlin et al., "A multicenter, double-blind, placebo-controlled trial of fenoldopam meysylate in the prevention of radiocontrast nephropathy in patients with moderate to severe renal insufficiency" Journal of the American Society of Nephrology, Vo. 11, Sep. 2000, p. 135A, XP009098223.

Tumlin, J.A. et al., Fenoldopam mesylate blocks reductions in renal plasma flow after radiocontrast dye infusion: a pilot trial in the prevention of contrast nephropathy:, Americal Heart Jouornal, vol. 143, No. 5, May 2002, pp. 894-903, XP002475379.

"FDA Form 510(K) on Related Correspondence for Advanced Equipment Development, Inc." Date Oct. 10, 1986.

Fox, S.L.; "Mechanisms of Contraction," Human Physiology, Fourth Edition, pp. 300-323. Date 1993.

Margulies, et al., Intra-Arterial Atrial Natriuetic Factor (ANF) Attenuates Radiocontrast-Induced etc., Renal Pathology, unknown date, pp. 666, Abstract only. Date 1991.

U.S. Appl. No. 09/165,333—Leschinsky, Boris—"Method and Apparatus for Treating Aneurysms" Date Oct. 11, 2001.

\* cited by examiner

BI-LATERAL LOCAL RENAL DELIVERY FOR TREATING CONGESTIVE HEART FAILURE AND FOR BNP THERAPY

CROSS-REFERENCES TO RELATED APPLICATIONS

This application claims the benefit of U.S. Provisional Application No. 60/571,057, filed May 14, 2004, the full disclosure of which is incorporated herein by reference. Further, the subject matter of this application is related to that of the following provisional, copending and published applications, the full disclosures of which are incorporated herein by reference, including 60/412,343; 60/412,476; 60/493,100; 60/502,468; 60/543,671; 60/550,632; 60/550,774; 60/508,751; 60/476,347; 60/479,329; 60/486,206; 60/486,349; 60/502,600; 60/502,389; 60/502,399; Ser. Nos. 09/229,390; 10/613,654; 09/562,493; 10/422,645; 10/438,176; 09/724,691; 10/422,624; 10/251,915; 10/636,359; 10/636,801; PCT/US03/21406; PCT/US03/29740; PCT/US04/08571; PCT/US03/29744; PCT/US03/29743; PCT/US03/29585; PCT/US03/29586; PCT/US00/00636; PCT/US01/13686; WO01/083016; WO2004/026370; WO2004/030718; WO2004/026371; WO2004/032791; and WO 2004/034767.

BACKGROUND OF THE INVENTION

I. Field of the Invention

This invention pertains generally to systems and methods for providing treatment to patients who are at risk for congestive heart failure and other conditions, and more particularly, to a system and method for treating related renal conditions through local delivery of agents to the renal system.

II. Description of Related Art

Heart failure is a leading cause of morbidity and mortality in the United States. There are more than 5 million patients with heart failure and over 500,000 newly diagnosed cases each year. The proper function of the kidney is directly related to cardiac output and blood pressure. In patients with congestive heart failure (CHF), cardiac output, blood pressure and renal function can be substantially compromised. Renal function can be further compromised during surgical intervention such as an angioplasty, coronary artery bypass, valve repair and/or replacement, and the like. Additionally, a patient undergoing less invasive analogs of these procedures can be particularly susceptible to renal damage from contrast imaging.

Conventionally, patients with pulmonary edema and symptoms related to CHF are often treated via systemic administration of diuretics and/or vasodilators in order to reduce the load on the heart, increase kidney function, and reduce edema. However, since these patients already suffer from low cardiac output and related blood pressure and renal problems, these systemically administered agents can take a long time to achieve beneficial results, if any. At the same time, systemic side effects such as hypotension, which further compromise the patients, often lead to discontinued treatment prior to having a desired therapeutic effect.

Acute renal failure ("ARF") is the sudden and temporary loss of kidney function. As such, there is an abrupt decrease in the kidney's ability to excrete waste from the blood. The change in kidney function can be attributable to many causes. Any traumatic event, such as hemorrhage, gastrointestinal fluid loss, or renal fluid loss without proper fluid replacement may cause a patient to exhibit ARF. Patients also become prone to developing ARF after receiving anesthesia, invasive surgery, or alpha-adrenergic agonists because of related systemic or renal vasoconstriction. Additionally, systemic vasodilation caused by anaphylaxis, anti-hypertensive drugs, sepsis or a drug overdose may also cause ARF. This response is likely because the body's natural defense is to temporarily shut down non-essential organs such as the kidneys; however, in the case of chronic CHF, the reduction in blood flow to the kidneys is not just temporary. Reduced cardiac output can be caused by cardiogenic shock, pericardial tamponade, massive pulmonary embolism, or the like. Notably, reduced cardiac output creates an excess of fluid in the body, which, in turn, can exacerbate CHF. More specifically, a reduction in blood flow and blood pressure in the kidneys (i.e., due to reduced cardiac output) can result in the retention of excess fluid in the body, leading, for example, to pulmonary and systemic edema. As such, there is a strong correlation between ARF, reduced cardiac output and CHF.

Various diagnostic systems and procedures employ local delivery of dye (e.g., radiopaque "contrast" agents) or other diagnostic agents that permit the external monitoring system to gather important physiological information about the patient. Patients that undergo diagnostic imaging and/or treatment procedures are usually exposed to these contrast agents or media. For example, angiography employs a hollow, tubular catheter for locally injecting radiopaque dye into a blood vessel or chamber, including coronary arteries in the case of coronary angiography, or a ventricle in the case of cardiac ventriculography. The kidneys are the body's main blood filtering tools and can be damaged from excessive exposure to high-density radiopaque contrast dye, such as during coronary-, cardiac-, or neuro-angiography procedures. These procedures can result in a condition known as radiocontrast nephropathy (RCN), wherein an acute impairment of renal function follows exposure to radiographic contrast materials. This typically results in a rise in serum creatinine levels of more than 25% above baseline, or an absolute rise of 0.5 mg/dl, within 48-72 hours. Hence, in addition to congestive heart failure (CHF), renal damage associated with RCN is a frequently observed cause of ARF. RCN is one of the most common causes of onset renal failure and renal impairment in hospital patients.

For prolonged local administration of protective agents into the renal system long dwell times may also be desirable. This can be achieved via a retrograde femoral approach, such as that commonly used in intravascular catheterization procedures. However, an antegrade approach, for example, via the brachial or radial arteries, may be more effective under specific circumstances (i.e., where a patient is not able to lay down during long dwell times due to pulmonary edema). The antegrade approach is gaining more popularity in standard coronary and other intravascular intervention, and may be particularly beneficial over femoral delivery in such cases as mentioned above where a patient will need to be able to sit up after placement of the device. Notably, when a patient is in motion during dwell periods, conventional catheter-based devices can become dislodged. For example, dislodging of a device placed in the renal arteries can occur during arm and upper body motion if placed via a brachial approach; or during leg, waist or lower body motion (such as simply sitting up after placement) if placed via a femoral approach.

Angiographic catheters and other tubular delivery catheters can be used to locally inject therapeutic agents into specific spaces and lumens into the body of CHF patients. Examples include local delivery of thrombolytic drugs such as TPA™ agent, heparin, cumadin, or urokinase into areas of vascular injury including thrombotic stroke, acute myocardial infarction, or near thrombogenic implants. In addition, various balloon catheter systems can be used for local administration of therapeutic agents into targeted body lumens or spaces associated with blood vessels. Balloon catheter systems may include balloons with porous or perforated walls that elute drug agents into surrounding tissue including walls of blood vessels. Multiple balloon catheters employ spaced balloons that are inflated to engage a lumen or vessel wall in order to isolate the intermediate catheter region from in-flow or out-flow across the balloons. A fluid agent delivery system can be coupled to the intermediate catheter region in order to fill the region with a drug. The drug is meant to affect the isolated region between the balloons.

There are some advances in the understanding of the pathophysiologic mechanisms contributing to sodium and water retention in CHF, and patients can be treated with a variety of drugs. Natriuretic peptides are a group of naturally occurring substances that act in the body to oppose the activity of the renin-angiotensin system. There are three major natriuretic peptides: atrial natriuretic or A-type peptide (ANP), which is synthesized in the atria; brain natriuretic or B-type peptide (BNP), which is synthesized in the ventricles; and C-type natriuretic peptide (CNP), which is synthesized in the brain. ANP and BNP act mainly as cardiac hormones while CNP is mostly active in the central nervous system and in peripheral tissues, including blood vessels. The natriuretic peptides ANP and BNP are also known as cardioneurohormones, and are secreted from the heart in response to increased intracardiac volume or pressure. They are secreted from the ventricles in response to volume expansion or pressure overload, and levels of BNP have been shown to be elevated in patients with left ventricular dysfunction. More specifically, both ANP and BNP are released in response to atrial and ventricular stretch, and will cause vasorelaxation, inhibition of aldosterone secretion in the adrenal cortex, and inhibition of renin secretion in the kidney. Both ANP and BNP will cause natriuresis and a reduction in intravascular volume, effects amplified by antagonism of antidiuretic hormone (ADH). For example, the natural human peptide called human B-type natriuretic peptide (HBNP) is secreted by the heart as part of the body's normal response to heart failure. The drug Natrecor® formulation (nesiritide) (manufactured by Scios Inc.) is a recombinant form of the endogenous human peptide which is intravenously administered to patients with acutely decompensated congestive heart failure (see Natrecor® (nesiritide) for Injection, Scios Inc. and U.S. Pat. Nos. 5,114,923 and 5,674,710). The physiologic effects of CNP are different from those of ANP and BNP. CNP has a hypotensive effect, but no significant diuretic or natriuretic actions. Three natriuretic peptide receptors (NPRs) have been described that have different binding capacities for ANP, BNP, and CNP. Removal of the natriuretic peptides from the circulation is affected mainly by binding to clearance receptors and enzymatic degradation in the circulation. Increased blood levels of natriuretic peptides have been found in certain disease states, suggesting a role in the pathophysiology of those diseases, including congestive heart failure (CHF), systemic hypertension, and acute myocardial infarction. The natriuretic peptides also serve as disease markers and indicators of prognosis in various cardiovascular conditions. BNP, which is synthesized in the cardiac ventricles and correlates with LV pressure, amount of dyspnea, and the state of neurohormonal modulation, makes this peptide the first potential marker for heart failure. Measurement of plasma BNP concentration is evolving as a screening technique (e.g., Biosite Diagnostics, Inc.) for identifying patients with various cardiac abnormalities regardless of etiology and degree of LV systolic dysfunction that can potentially develop into obvious heart failure and carry a high risk of a cardiovascular event (Dr. James Hill, Natriuretic Peptides in Heart Failure, University of Florida College of Medicine (2001)).

Patients suffering from CHF would enormously benefit from safe and effective local therapies or prophylaxis of renal conditions related to CHF. Clearly, there exists a clinical need for treatment that provides for a fluid overload reduction quickly, reliably, and in the absence of undesired side effects. This is particularly critical, since the CHF patient population often presents with pulmonary edema and many other serious co-morbidities. A further need exists for a bilateral renal delivery device system and method that would allow for reliable and robust positioning of the bilateral delivery/injection assembly in vivo. Such a system would work regardless of whether the patient is motion or not.

BRIEF SUMMARY OF THE INVENTION

One aspect of the invention provides a system and method for treating congestive heart failure (CHF) using an in-dwelling bilateral local renal delivery catheter that is adapted to maintain the position of a bilateral local renal injection assembly at an injection location associated with the renal arteries, and during relative patient motion between an access site and the injection location.

Another aspect of the invention provides a system and method for bilateral local renal delivery of an agent that affects renal function in a living being in a manner that achieves substantial renal concentrations or effects and with substantially lower systemic concentrations or effects.

Still, another aspect of the invention provides a system and method for bilateral local renal delivery of BNP in a living being in a manner that achieves substantial local renal concentrations or effects and with substantially lower levels of systemic concentrations or effects.

A further aspect of the invention provides for a method that comprises locally administering a natriuretic peptide into at least one renal artery of a patient. Alternatively, the natriuretic peptide can be locally delivered into both renal arteries of the patient, wherein the local delivery into both renal arteries can occur simultaneously.

The invention further contemplates a method that comprises positioning an intravascular catheter through an aorta so that at least one delivery port is positioned in or about at least one renal artery, and delivering an active substance through the intravascular catheter to the renal artery or arteries, wherein the catheter comprises a compliant region which accommodates tension or compression resulting from patient movement at the catheter access site when the catheter is positioned in the aorta and the delivery port is in or about the renal artery or arteries.

The invention also encompasses a renal drug delivery catheter that comprises a catheter body having a proximal end, a distal end, and a drug delivery lumen therethrough, and a hub on the proximal end adapted to deliver drugs to the drug delivery lumen, wherein the distal end of the catheter body is adapted to enter a renal artery when the catheter body is located in an adjacent aorta, and wherein a portion of the catheter body is compliant and configured to accommodate tension or compression resulting from patient movement when the catheter body is in the aortic and the distal end is in the renal artery.

Another aspect of the invention provides for the use of a natriuretic peptide in the manufacture of a medicament for the therapeutic and/or prophylactic treatment of congestive heart failure or other conditions, including but not limited to, dyspnea, elevated pulmonary capillary wedge pressure, chronic renal insufficiency, acute renal failure, cardiorenal syndrome, and diabetes mellitus. The invention further provides for the use of a natriuretic peptide in the manufacture of a medicament for the therapeutic and/or prophylactic treatment of renal conditions that are associated with congestive heart failure or any or all of the conditions described above. The natriuretic peptide is locally administered into at least one renal artery of a patient. Alternatively, the natriuretic peptide can be locally administered into both renal arteries of the patient, wherein the local administration into both renal arteries can occur simultaneously.

Another aspect of the invention provides for the use of a natriuretic peptide in the preparation of an agent in ready-to-use drug form for treating or preventing congestive heart failure or other conditions, including but not limited to, dyspnea, elevated pulmonary capillary wedge pressure, chronic renal insufficiency, acute renal failure, cardiorenal syndrome, and diabetes mellitus. The invention further provides for the use of a natriuretic peptide in the preparation of an agent in ready-to-use drug form for treating or preventing renal conditions that are associated with congestive heart failure or any or all of the conditions described above.

Various further aspects, modes, embodiments, variations, and features of the invention will be brought out in the following portions of the specification, wherein the detailed description is for the purpose of fully disclosing particular illustrative embodiments of the invention without placing limitations thereon.

BRIEF DESCRIPTION OF THE DRAWINGS

The present invention is best understood when read in conjunction with the accompanying figures, which serve to illustrate the preferred embodiments. It is understood, however, that the invention is not limited to the specific embodiments disclosed in the figures.

DETAILED DESCRIPTION OF THE INVENTION

I. Definitions

Figure 1A:
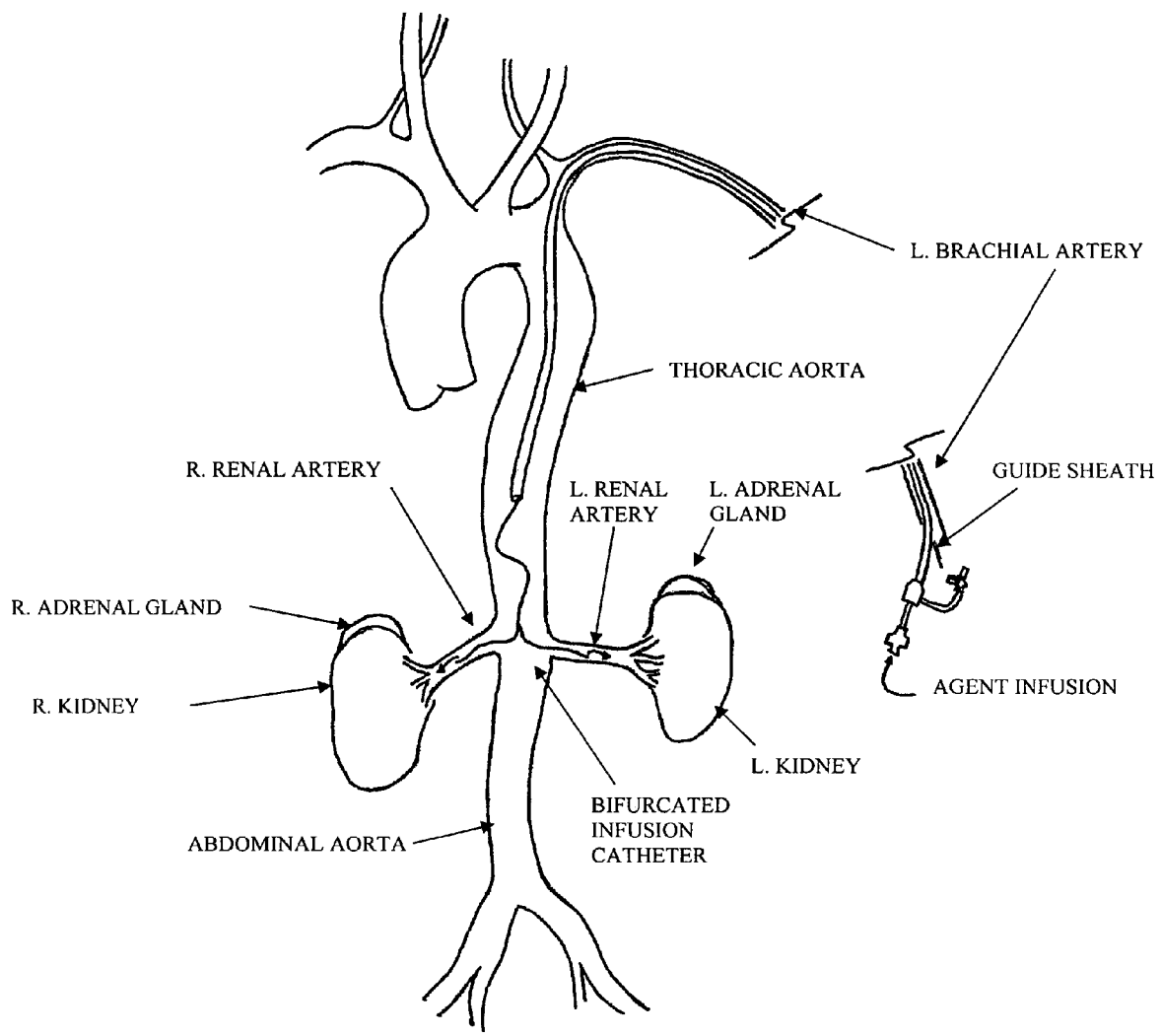
FIG. 1A depicts one embodiment of the invention, a bifurcated infusion catheter intended for antegrade delivery to the renal arteries, with a flexible shaft of suitable length for brachial artery access and a randomly shaped compliant section.
Figure 1B:
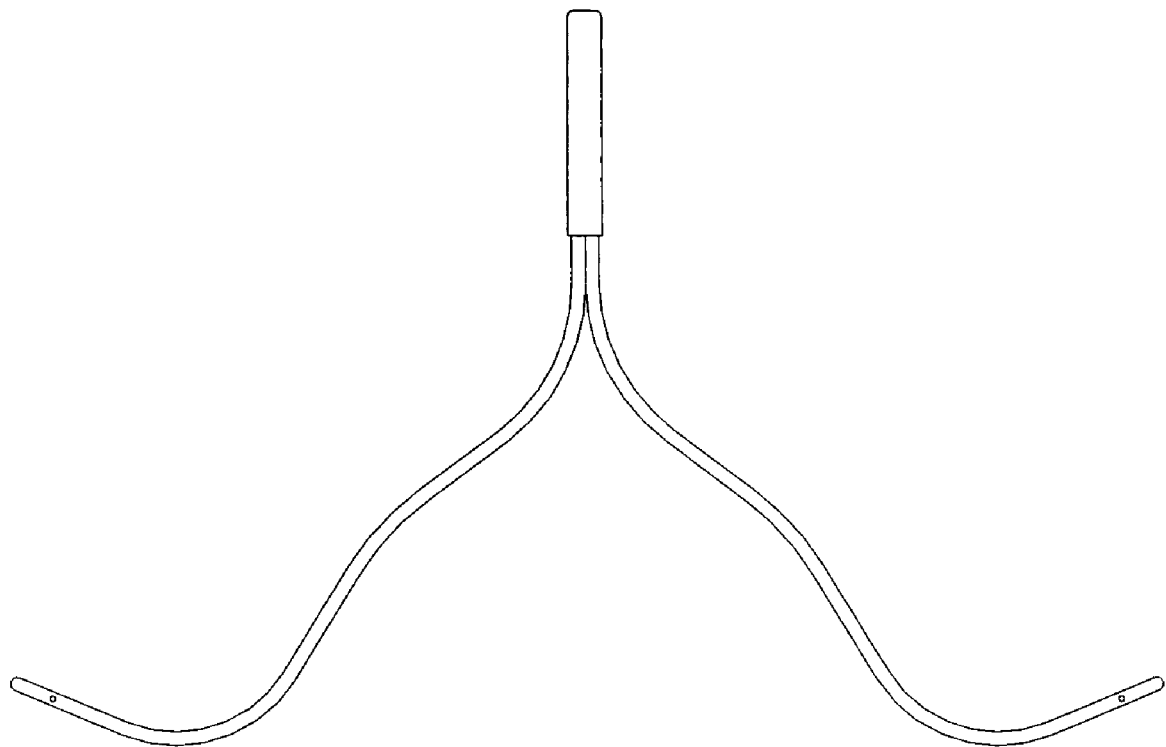
FIG. 1B depicts another embodiment of a bifurcated infusion branch configuration for the antegrade catheter as demonstrated in FIG. 1A.
Figure 1C:
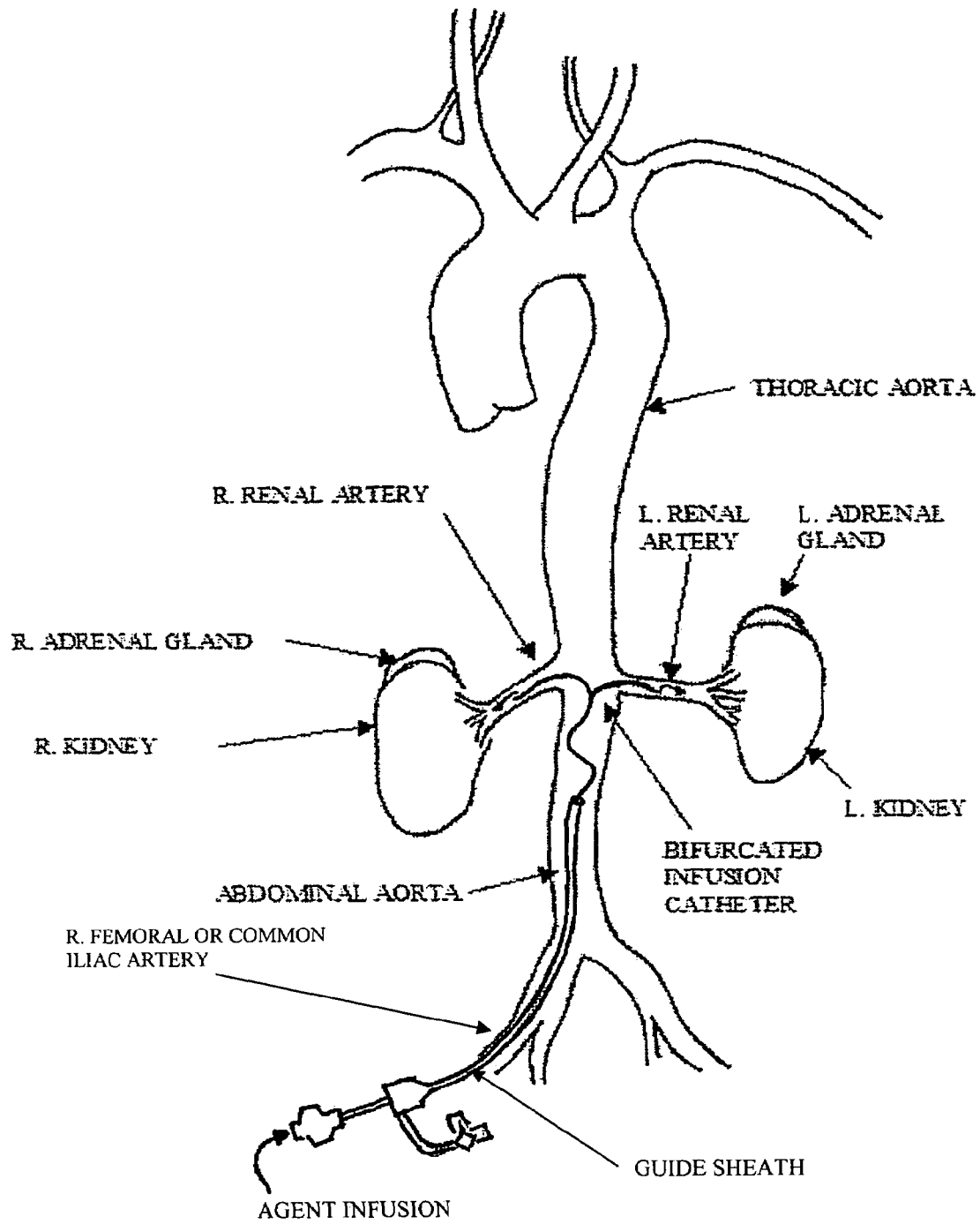
FIG. 1C depicts a further embodiment of the invention, a bifurcated infusion catheter intended for retrograde delivery to the renal arteries, with a flexible shaft of suitable length for femoral or iliac artery access and a randomly shaped compliant section.
Figure 1D:
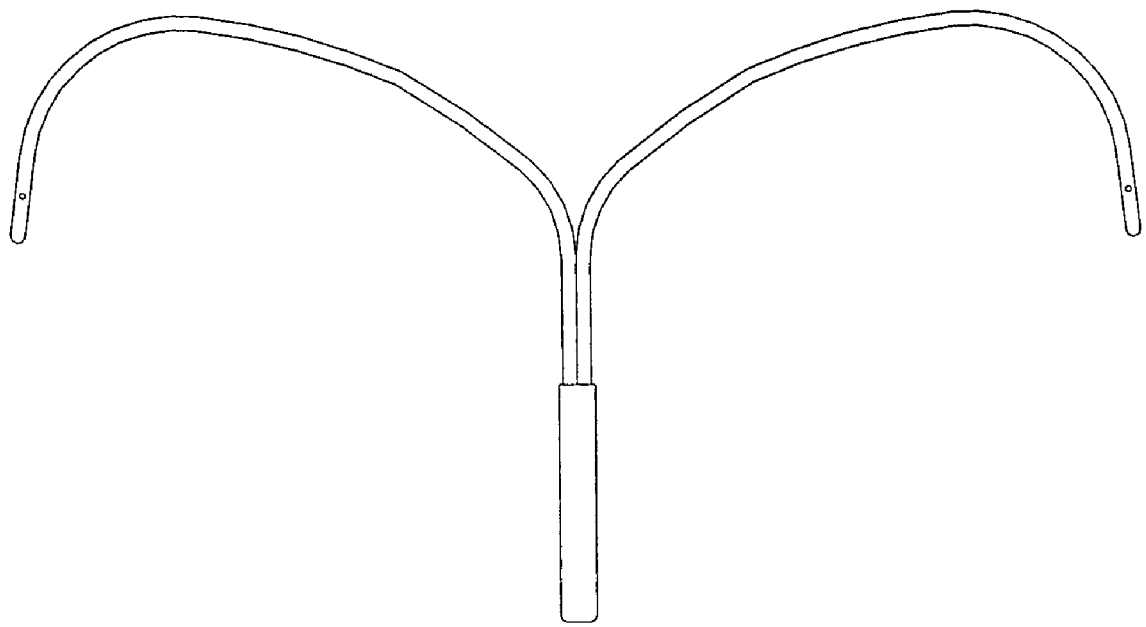
FIG. 1D depicts a further embodiment of a bifurcated infusion branch shape for the retrograde catheter as demonstrated in FIG. 1C.

The following definitions are set forth to illustrate and define the meaning and scope of the various terms used to describe the present invention.

A "natriuretic peptide" refers to a natural or artificial substance that can be administered to a subject that is at risk for developing or suffering from one or more condition, including, but not limited to congestive heart failure, dyspnea, elevated pulmonary capillary wedge pressure, chronic renal insufficiency, acute renal failure, cardiorenal syndrome, and diabetes mellitus. The natriuretic peptide can administered via a pharmaceutical carrier, in a pharmaceutical compositions, in form of a drug, as an agent or via other suitable means. Examples of natriuretic peptides are atrial natriuretic or A-type natriuretic peptide (ANP), brain natriuretic or B-type natriuretic peptide (BNP), and C-type natriuretic peptide (CNP).

The term "compliant region", as used herein, refers to a portion of a catheter or other similar device. The compliant region accommodates tension or compression resulting from patient movement when a catheter or similar device is positioned inside of the patient. This may be accomplished by the catheter having a specific section wherein the forces required to stretch or compress the section's length are substantially less than those required to displace the catheter at its renal location or at its vascular access site; the section may be formed of a more compliant material than the remainder of the catheter in order to achieve this behavior. Alternatively, this may be accomplished via providing a pre-set or random shape to a section of the catheter shaft, the provision of which will effect a similar ability to isolate movement from one end of the catheter to the other, preventing dislodgment of the catheter from its renal location. Examples of the latter type of compliant region include, but are not limited to, structures that have a coil, a serpentine, or a zig-zag geometry, and in these cases the material properties of the compliant region may be the same, similar, or different than those of the remainder of the catheter.

The term "active substance", as used herein, refers to any agent, drug, and/or pharmaceutical composition that can be administered to a subject, including animals and humans. The active substance can be naturally derived or synthetically manufactured.

II. Bi-Lateral Local Renal Delivery

One aspect of the invention provides for a method that comprises locally administering a natriuretic peptide into at least one renal artery of a patient. Alternatively, the natriuretic peptide can be locally delivered into both renal arteries of the patient, wherein the local delivery into both renal arteries can occur simultaneously. Local renal artery infusion is preferable over standard IV administration as the renal dose can be maximized while concurrently the systemic exposure is reduced due to the first-pass elimination effects of the kidneys. This method is particularly applicable when the patient is at risk of developing and/or suffers from at least one condition including, but not limited to, congestive heart failure, dyspnea, elevated pulmonary capillary wedge pressure, chronic renal insufficiency, acute renal failure, cardiorenal syndrome, and diabetes mellitus, and when the patient is resistant to IV therapy due to systemic dosing limitations or side effects. Preferably, the peptide is administered in form of a drug or pharmaceutical composition. In one embodiment, the drug is delivered in bolus form at a dosage of about 1 to 5 mcg/kg. In another embodiment, the drug is delivered via continuous administration at a dosage of about 0.005 to 0.05 mcg/kg/min. In yet another embodiment, the drug is delivered through a bolus form at a dosage of about 1 to 5 mcg/kg in combination with continuous administration at a dosage of about 0.005 to 0.05 mcg/kg/min. The natriuretic peptide administered to the patient includes BNP, ANP, and CNP, or a combination of one or more of these. The administration of the natriuretic peptide may be adjusted depending on various factors, such as clinical condition of the patient, age of the patient, severity of the disease, environmental factors, etc. For example, a patient suffering from moderate to severe symptoms of CHF can be administered natriuretic peptide in form of a bolus at, for example, 2 mcg/kg bolus followed by a 0.01 mcg/kg/min infusion. The dose is adjustable and the infusion dose can be increased or decreased as necessary to achieve the desired effects. Alternatively or in combination, an additional bolus dose could also be given.

The invention further contemplates a method that comprises positioning an intravascular catheter through an aorta so that at least one delivery port is positioned in or about at least one renal artery, and delivering an active substance through the intravascular catheter to the renal artery or arteries, wherein the catheter comprises a compliant region which accommodates tension or compression resulting from patient movement when the catheter is positioned in the aorta and the delivery port is in the renal artery or arteries. The compliant region of the catheter is preferably non-linear and includes, but is not limited to, a coil structure, a serpentine structure, or a zig-zag structure. Such a structure allows that section of the catheter to absorb motion like a spring, allowing the renal delivery portion of the catheter to remain in its location for agent delivery while the patient is mobile. In addition, the compliant region of the catheter may have a stiffness less that than of adjacent regions to permit slackness in the region after deployment in the aorta. In one embodiment, the positioning of the intravascular catheter comprises straightening the compliant region with a stylet disposed within a lumen of the catheter, advancing the catheter through the aorta while the catheter remains straightened with the stylet, and withdrawing the stylet from the compliant region to allow the compliant region to assume its non-linear configuration. The active substance that is delivered via this method comprises a natriuretic peptide (e.g., BNP, ANP, and CNP). The method may further include delivering the natriuretic peptides at specific dosages. As indicated above, the natriuretic peptide can be delivered in bolus form at a dosage of about 1 to 5 mcg/kg, via continuous administration at a dosage of about 0.005 to 0.05 mcg/kg/min, and/or through a bolus form at a dosage of about 1 to 5 mcg/kg in combination with continuous administration at a dosage of about 0.005 to 0.05 mcg/kg/min. Related systems and methods are disclosed in co-pending commonly owned PCT International Patent Application Nos. PCT/US03/29744 and PCT/US04/08573, the disclosures of which are incorporated herein by reference in their entirety.

III. Local Renal Delivery System

The invention also encompasses a renal drug delivery catheter that comprises a catheter body having a proximal end, a distal end, and a drug delivery lumen therethrough, and a hub on the proximal end adapted to deliver drugs to the drug delivery lumen, wherein the distal end of the catheter body is adapted to enter a renal artery when the catheter body is located in an adjacent aorta, and wherein a portion of the catheter body is compliant and configured to accommodate tension or compression resulting from patient movement when the catheter body is in the aorta and the distal end is in the renal artery. The portion of the catheter body that is compliant and configured to accommodate tension or compression is preferably non-linear and includes, but is not limited to, a coil, a serpentine, or a zig-zag geometry over a length. In addition, the compliant section or portion may have a stiffness that is less than that of adjacent regions of the catheter so that the complaint section is slack and can be loosely deployed to accommodate tension and elongation after placement. In one embodiment, the renal drug delivery catheter further comprises a stylet, which can be placed in a lumen during delivery to straighten the compliant section or portion.

One embodiment of the invention provides a bifurcated renal infusion catheter. The catheter can be placed bilaterally into the renal arteries via the aorta to infuse any given agent or drug directly into the renal circulation. This simultaneously achieves the desired renal effect and the reduction or elimination of systemic side effects. This embodiment is illustrated in FIG. 1, wherein the bifurcated infusion catheter consists of a flexible shaft of a usable length, which can be, for example, between about 70 cm to approximately 160 cm long, with an outer diameter within a range, for example, of between about 2 Fr. to about 6 Fr., with two distal infusion branches. Each infusion branch includes a generally flexible tubular construction with an outer diameter that may typically be in the range for of between about 1 Fr. to about 3 Fr. The two branches may be generally opposed, such as for example by about 180°, so as to aid in bilateral renal artery cannulation. The branches can be desirably shaped in order to aid with a specific anatomy. Composite construction (e.g., coiled or braided extruded polymers and/or co-extrusions) of the shaft and infusion branches may be employed in order to take advantage of other embodiments including flexibility, column strength, and torque response. The branches themselves can be cylindrical or may have non-circular cross-sections. The distal (working) end of the device is can be constructed from materials that are visible under fluoroscopy. Alternatively, such materials may be incorporated or placed in or on the device so as to aid in placement under fluoroscopic guidance. The proximal end of the shaft is generally adapted to couple to a fluid source. The device is further adapted for fluid delivery from the source outside the patient and directly into the renal vasculature. The coupler may take the form of an industry-standard luer fitting or other forms as needed.

With the bifurcated renal infusion catheter, arterial access is gained via the brachial artery by using standard techniques (i.e., Seldinger). As such, a standard, commercially available guiding catheter (e.g., about 6-8 Fr.) or guide sheaths (e.g., about 4-6 Fr.) can be placed through the access and guided in retrograde fashion to the aortic arch via fluoroscopy. The guiding catheter or guide sheath is advanced into the perirenal aorta in an antegrade manner. Through this guiding catheter or guide sheath the bifurcated infusion catheter is then delivered and placed into the renal arteries bilaterally. This device provides for a quick and simple bilateral renal artery cannulation and placement. Once the infusion catheter has been placed, infusion of any given substance (e.g., drug, solution, etc.) can begin according to a physician's direction. Optionally, the device could be introduced through a different artery, for example, the radial artery, depending on preference. Advantages to the use of a guide sheath over a guiding catheter are that it can serve as the access sheath as well, eliminating the need for a third device (introduction sheath) as would be required with the guiding catheter approach, and, as such, this may allow for a reduced profile a the vessel entry site.

Figure 2:
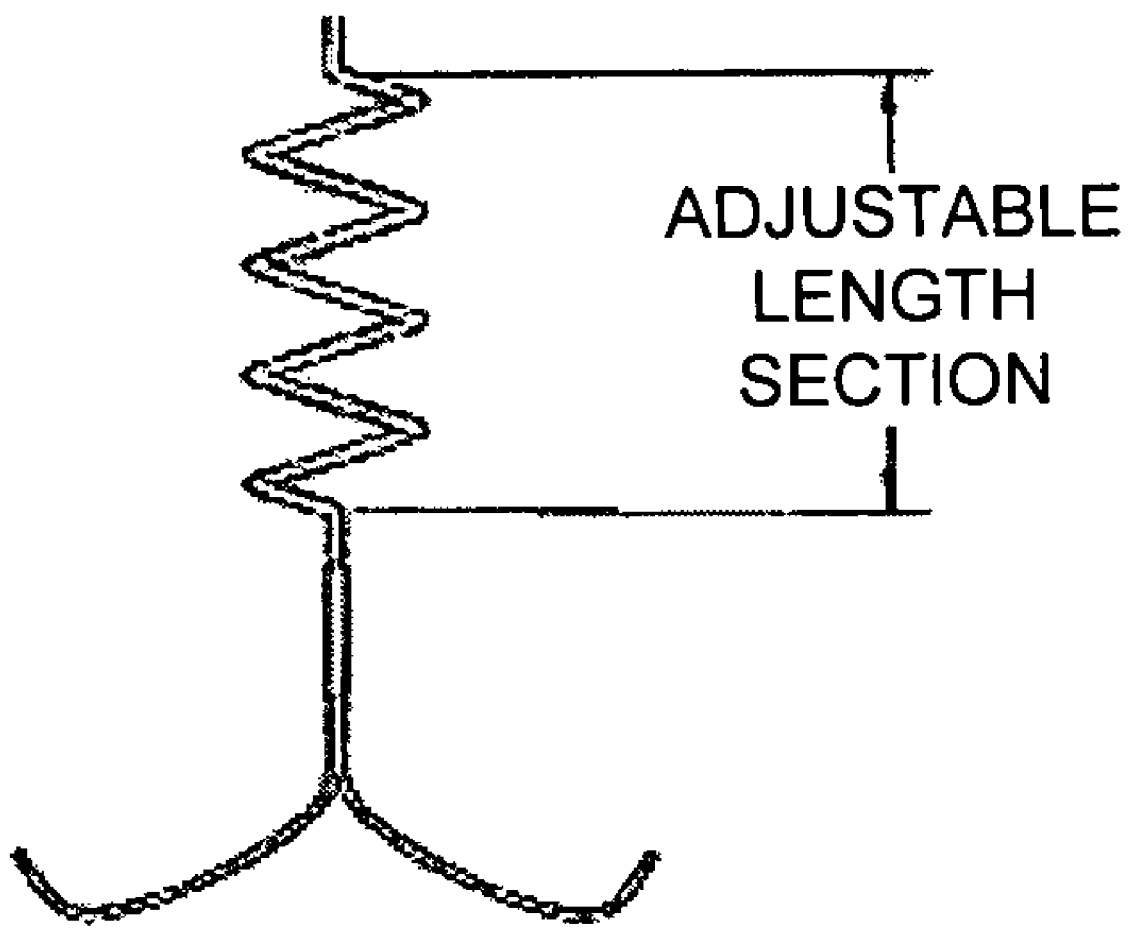
FIG. 2 illustrates another embodiment of the invention, a catheter with a structured section in the form of a coil along a catheter shaft. This design accommodates patient movement without affecting renal placement of the catheter.

The catheter of the instant invention can include a mechanism or structure that can be incorporated within the device to absorb or otherwise accommodate patient movement. This prevents the displacement of the infusion branches from the renal arteries. In order to alleviate a patient's condition, the bifurcated infusion catheter as described may be placed into the patient for an extended period of time (e.g., 4-12 hours or longer). The patient may not remain perfectly still during all of this time, thus, a mechanism that prevents displacement of the device is beneficial and a novel feature of this invention. Accordingly, one embodiment provides a specifically structured section (e.g., a compliant region) of the device for accommodating patient movement without branch dislodgement. The compliant region accommodates tension or compression resulting from patient movement when the catheter is positioned in the aorta. The compliant region can be non-linear and includes, but is not limited to, a coil structure, a serpentine structure, or a zig-zag structure. This compliant region (e.g., a movement-absorbing structure) can be placed, for example, just proximal of the bifurcated infusion branch portion of the catheter. This type of structure allows the device to change length and bend as needed, so that the infusion branches stay in the renal arteries as placed. In one embodiment, the compliant region comes in the form of a loose coil or wave along the catheter shaft. This structure takes shape once deployed in the patient, and can accommodate patient movement without affecting renal placement. An example of this type of pre-formed structure is shown in FIG. 2. Alternatively, this coil or wave may be of a random nature, formed after placement of the device in the patient. The inclusion of a compliant region as described, could in some instances interfere with the handling characteristics of the device, in particular when force transfer is desired, such as during branch seating. Therefore, another structure, such as a mandrel or a stylet provides for the required column strength and torque response to allow for device placement into the renal arteries. A mandrel or a stylet can be placed into the device's fluid lumen to aid in the handling response. The inclusion of a mandrel or stylet aids in keeping the device in a straight configuration, and thus, aids in the axial handling response (push, pull) by providing column strength. A mandrel and its corresponding lumen may be of a non-circular cross section, so as to also provide a mechanism for transmitting torque along the length of the device (whereas a standard round mandrel in a round lumen may simply spin without transmitting torque). In another embodiment, the mandrel or stylet is bifurcated in a similar geometric fashion as the catheter, such that the mandrel or stylet extends into both infusion branches simultaneously, and thus, torque can be transmitted in that manner. If placed in the fluid lumen, a stylet may be removed as necessary to allow agent infusion into the renal arteries.

Additional embodiments of the device and associated method as described above are included herein. For example, a device may be designed to be delivered from below, i.e., via a retrograde femoral approach, and thus, the dimensions, overall construction, and infusion branch shape may be altered to better suit this use. The access into the brachial artery (and approach from this point to the renal arteries) is usually preferred in patients with pulmonary edema subsequent to CHF. In this case the device's dimension, overall construction, and infusion branch shape are tailored for brachial delivery and the antegrade approach. Usually, the device is placed with the patient while he or she is lying down. During infusion times, these patients may not be able tolerate lying down (i.e., flat) for the entire length of time because of the high amount of fluid in their lungs. Thus, these patients may need to sit up in order to properly breathe. Consequently, a standard femoral or iliac approach can be difficult in these patients since the access for the device is within the crease of the groin. When the patient is sitting up, device dislocation can occur. In order to address this issue, a motion-absorbing structure such as the one described previously (e.g., compliant region) or one of another form that serves a similar purpose may be employed to allow the device to adapt to the patient's vasculature during movement. The device's infusion branches could incorporate an additional fixation mechanisms or features to hold the infusion branches in the renal arteries. This allows for substantial blood flow across the point of fixation such that the baseline renal artery flow is not compromised and any agents and/or drugs are efficiently administered. Furthermore, any materials, preferred coatings, dimensions, and the like can be adjusted to various clinical needs and/or physicians' preferences and, thus, are considered to be within the scope of this invention.

Another embodiment of the invention provides for a method wherein the bifurcated catheter remains substantially inside of the guiding catheter or guide sheath during placement. More specifically, only the distal infusion branches are deployed from the guiding catheter or guide sheath. The various other maneuvers that are usually required for placement of the catheter are carried out by maneuvering the guiding catheter or guide sheath. The flexible, motion-absorbing section of the bifurcated infusion catheter is not exposed until after the branches are placed in the renal arteries. Modifications to this method to allow for effective maneuvering of a flexible portion of the catheter are considered within the scope of the invention.

The bifurcated local renal infusion devices of the instant invention are useful in animals and humans, particularly for the infusion of agents and drugs into the peripheral vasculature, including the renal arteries. The device has been successful in both animal (see Examples) and human models. It has proven to be particularly effective whenever it is necessary to quickly access the renal arteries bilaterally and deliver agents or drugs into the renal vasculature selectively, and without eliciting any unwanted side effects. For example, in the canine model, the device was used to evaluate intrarenal (IR) infusion of Natrecor® agent (B-type natriuretic peptide or BNP, see Scios Inc., Johnson & Johnson). A pharmacokinetic study in two dogs (see Examples below) demonstrated significantly reduced steady-state levels of plasma BNP when a given dose was administered IR versus systemically (IV) (i.e., the average reduction was 63%). This shows a significant first-pass clearance effect of BNP by the kidneys and, thus, may serve to increase the maximum usable dose. Clinically, the main side effect of BNP has been that systemic hypotension often limits the dose, and/or time a dose can be given, thereby reducing the efficacy of the drug. Through this animal work, it has been shown that IR delivery of BNP results in reduced systemic levels when compared to IV delivery of BNP, and thus, proportionately reduces the occurrence of side effects like hypotension. A more detailed description of the studies and the related in vivo observations follows in the Example section.

Other devices or methods, including pharmaceutical preparations or dosing or delivery regimens, and medical therapeutic or prophylactic procedures, are also contemplated herein.

IV. Examples

The following specific examples are intended to illustrate the invention and should not be construed as limiting the scope of the claims. The examples provide a summary of a pre-clinical investigation of the hypotensive effects and pharmacokinetics of intra-renal (IR) versus intravenous (IV) administration of a B-type natriuretic peptide in the canine model.

(i) PURPOSE

The purpose of the experiments was to demonstrate the pharmacokinetics and certain other effects of a novel means of administration (intra-renal, IR) of B-type natriuretic peptide (BNP) versus standard intravenous (IV) administration. The experimental hypothesis was that IR administration of the natriuretic peptide would result in reduced systemic exposure (as measured by serum BNP levels) and, thus, reduced systemic side effects (e.g., hypotension), afforded by the kidneys' first-pass elimination of the peptide.

(ii) EXPERIMENTAL PROTOCOL

IR versus IV administration of human recombinant BNP (Natrecor® agent, Scios, Inc., Johnson & Johnson) was compared in the canine model (two animals). IR infusion was achieved using the FlowMedica Benephit™ Infusion System (FlowMedica, Inc.). IV and IR administration was performed in each animal sequentially, and the administration periods were separated by five days to allow for washout and re-acclimation of the animals. IV administration was conducted on the first day in both animals. Other than the route of BNP administration, all other parameters were identical between the IV and IR administration days in both dogs.

Canine #1 received a 2 mcg/kg/min bolus of BNP followed immediately by a 0.15 mcg/kg/min BNP infusion for 90 minutes, followed by a 2-hour washout period. Then vasoconstriction was induced via phenylepherine until mean arterial pressure (MAP) was increased by approximately 30% (approximately 1 hour), and then BNP was again administered at 0.15 mcg/kg/min for 90 minutes.

Canine #2 received a 2 mcg/kg/min BNP bolus followed immediately by a 4-hour continuous infusion of BNP at 0.15 mcg/kg/min.

Key endpoints included serum levels of BNP (pharmacokinetics, both animals) following IR and IV BNP administration, and blood pressure response in response IR and IV BNP administration (Canine #1 only).

(iii) RESULTS

Figure 3:
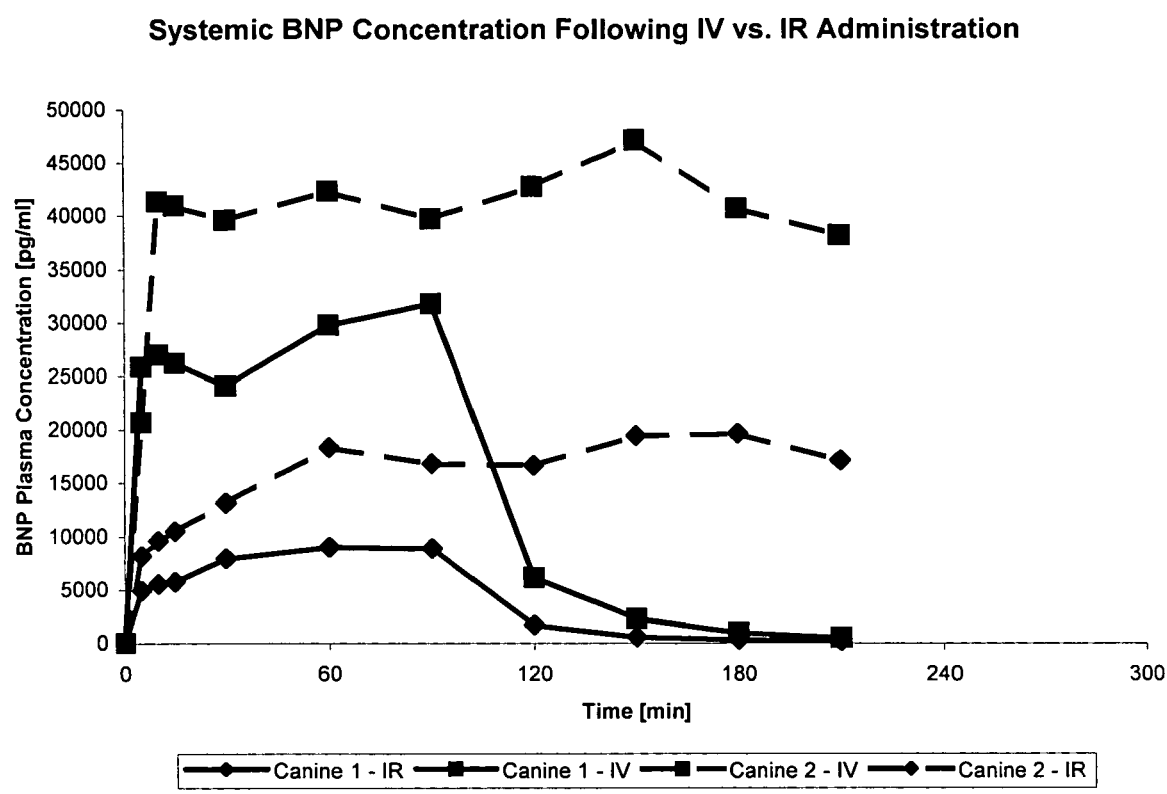
FIG. 3 depicts a graph that shows the systemic BNP concentration in two different test animals as a result of intra-renal (IR) vs. intravenous (IV) administration of BNP. Differences of 75% and 66%, and 61% and 69% in serum BNP levels were seen with IR (▼) versus IV (■) infusion of BNP at comparable time points in Canine #1 (solid lines) and Canine #2 (broken lines), respectively.

The mean difference between serum BNP levels at comparable time points associated with IR and IV infusion was 75% and 66%, and 61% and 69% in Canine #1 and Canine #2, respectively (higher with IV administration in both cases). See FIG. 3.

Figure 4A:
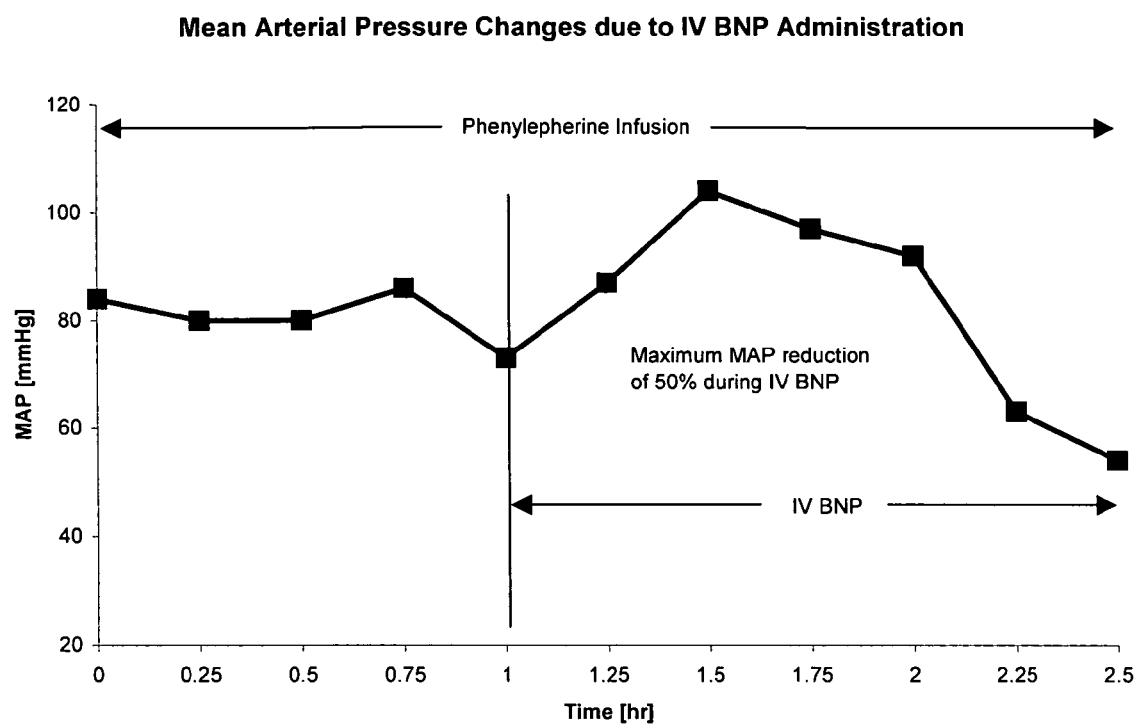
FIG. 4A depicts a graph that shows the mean arterial pressure changes due to intravenous (IV) BNP administration. A maximum BP reduction of 50% with IV BNP administered during constricted vascular state induced by phenylepherine demonstrated an anti-vasoconstrictive effect of BNP.
Figure 4B:
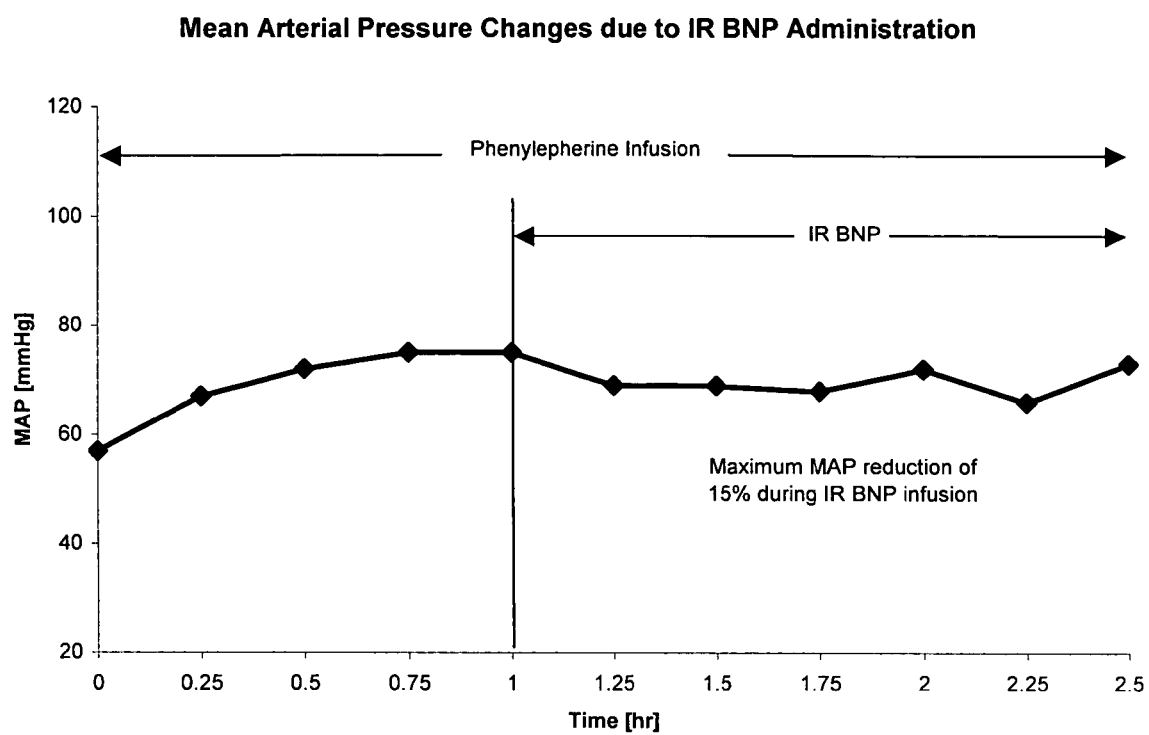
FIG. 4B depicts another graph that shows the mean arterial pressure changes to intra-renal (IR) BNP administration. A maximum BP reduction of 15% with IR BNP administered during constricted vascular state induced by phenylepherine is shown. The relative lack of effect on MAP as compared to IV administration demonstrated the effect of lower systemic BNP levels due to IR administration and renal first-pass effects.

In Canine #1, a 50% maximum reduction in MAP was observed with IV BNP administration adjunctive to phenylepherine administration, whereas a maximum reduction of only 15% was seen with IR BNP administration in the presence of artificially-increased MAP via phenylepherine. See FIGS. 4A and 4B. The relative lack of effect on MAP as compared to IV administration demonstrated the effect of lower systemic BNP levels due to IR administration and renal first-pass effects.

(iv) CONCLUSIONS

IR administration of BNP resulted in approximately 61-75% lower systemic levels than the IV administration of the same dose; thus, a significant renal first-pass effect was demonstrated in keeping with the experimental hypothesis. Also demonstrated was a decreased blood pressure effect, a 50% maximal reduction with IV administration versus a 15% maximal reduction with IR at the same dose, under similar baseline conditions of controlled MAP achieved via administration of phenylepherine. Based on these findings it is likely that IR administration of BNP (and other natriuretic peptides) allows for increased renal effects by increasing the local dose while at the same time reducing systemic side effects, because renal first-pass effects reduce systemic exposure to the drug. This provides a significant clinical benefit for patients for whom the effective dose is limited due to hypotensive or other side effects.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the claims. All publications, patents and patent applications cited in this specification are herein incorporated by reference in their entirety.

What is claimed is:

1. A method comprising:
    placing a bifurcated renal infusion catheter within a patient, such that a first distal infusion branch of the catheter is disposed within a first renal artery and a second distal infusion branch of the catheter is disposed within a second renal artery; and
    locally administering a natriuretic peptide into both renal arteries of the patient via the bifurcated renal infusion catheter,
    wherein the patient is at risk of developing or is suffering from at least one condition selected from the group consisting of congestive heart failure, dyspnea, elevated pulmonary capillary wedge pressure, chronic renal insufficiency, acute renal failure, cardiorenal syndrome, and diabetes mellitus.

2. The method as in claim 1, wherein the local delivery into both renal arteries occurs simultaneously.

3. The method as in claim 1, wherein the peptide is administered under conditions selected to reduce the risk of systemic side effects including hypotension.

4. The method as in claim 1, wherein the peptide is delivered in form of a drug or pharmaceutical composition.

5. The method as in claim 4, wherein the drug is delivered in bolus form at a dosage of about 1 to 5 mcg/kg.

6. The method as in claim 4, wherein the drug is delivered via continuous administration at a dosage of about 0.005 to 0.05 mcg/kg/min.

7. The method as in claim 4, wherein the drug is delivered through a bolus form at a dosage of about 1 to 5 mcg/kg in combination with continuous administration at a dosage of about 0.005 to 0.05 mcg/kg/min.

8. The method as in claim 1, wherein the natriuretic peptide is selected from the group consisting of BNP, ANP, and CNP.

9. The method of treating a patient comprising:
bilaterally cannulating both renal arteries of a patient with a bifurcated renal infusion catheter, such that a first distal infusion branch of the infusion catheter is disposed within a first renal artery of the patient and a second distal infusion branch of the infusion catheter is disposed within a second renal artery of the patient; and
locally administering a natriuretic peptide into both renal arteries of the patient via a bifurcated renal infusion catheter,
wherein the patient is at risk of developing or is suffering from at least one condition selected from the group consisting of congestive heart failure, dyspnea, elevated pulmonary capillary wedge pressure, chronic renal insufficiency, acute renal failure, cardiorenal syndrome, and diabetes mellitus.

10. The method as in claim 9, wherein the patient is at risk of developing at least one condition selected from the group consisting of congestive heart failure, dyspnea, elevated pulmonary capillary wedge pressure, chronic renal insufficiency, acute renal failure, cardiorenal syndrome, and diabetes mellitus.

11. The method as in claim 9, wherein the patient is suffering from least one condition selected from the group consisting of congestive heart failure, dyspnea, elevated pulmonary capillary wedge pressure, chronic renal insufficiency, acute renal failure, cardiorenal syndrome, and diabetes mellitus.

12. The method as in claim 9, wherein the peptide is administered under conditions selected to reduce the risk of systemic side effects including hypotension.

13. The method as in claim 9, wherein the peptide is delivered in form of a drug or pharmaceutical composition.

14. The method as in claim 13, wherein the drug is delivered in bolus form at a dosage of about 1 to 5 mcg/kg.

15. The method as in claim 13, wherein the drug is delivered via continuous administration at a dosage of about 0.005 to 0.05 mcg/kg/min.

16. The method as in claim 13, wherein the drug is delivered through a bolus form at a dosage of about 1 to 5 mcg/kg in combination with continuous administration at a dosage of about 0.005 to 0.05 mcg/kg/min.

17. The method as in claim 9, wherein the natriuretic peptide is selected from the group consisting of BNP, ANP, and CNP.

18. The method of treating a patient comprising:
locally administering a natriuretic peptide into both renal arteries of the patient via a bifurcated renal infusion catheter,
wherein the patient is at risk of developing or is suffering from at least one condition selected from the group consisting of congestive heart failure, dyspnea, elevated pulmonary capillary wedge pressure, chronic renal insufficiency, acute renal failure, cardiorenal syndrome, and diabetes mellitus.

19. The method as in claim 1, wherein the patient is suffering from acute renal failure.

20. The method as in claim 1, wherein the patient is at risk of developing acute renal failure.

21. The method as in claim 1, wherein the patient has a serum creatinine level above baseline.

22. The method as in claim 9, wherein the patient is suffering from acute renal failure.

23. The method as in claim 9, wherein the patient is at risk of developing acute renal failure.

24. The method as in claim 9, wherein the patient presents a percentage rise in serum creatinine of at least 25% or an absolute rise in serum creatinine of at least 0.5 mg/dl, or both, within 72 hours.

25. The method as in claim 18, wherein the patient is suffering from acute renal failure.

26. The method as in claim 18, wherein the patient is at risk of developing acute renal failure.

27. The method as in claim 18, wherein the patient presents a percentage rise in serum creatinine of at least 25% or an absolute rise in serum creatinine of at least 0.5 mg/dl, or both, within 72 hours.

* * * * *